United States Patent [19]

Seckinger et al.

[11] Patent Number: 5,482,921
[45] Date of Patent: Jan. 9, 1996

[54] HYDANTOIN COMPOUNDS

[75] Inventors: Karl Seckinger, Riegel, Germany; Karlheinz Milzner, Basel, Switzerland; Fred Kuhnen, Weil, Germany; Sasank S. Mohanty, Baden, Switzerland

[73] Assignee: Sandoz Ltd., Basel, Switzerland

[21] Appl. No.: 984,716

[22] Filed: Dec. 2, 1992

Related U.S. Application Data

[63] Continuation of Ser. No. 808,247, Dec. 12, 1991, abandoned.

[30] Foreign Application Priority Data

Dec. 18, 1990 [GB] United Kingdom .................. 9027426
Jun. 4, 1991 [GB] United Kingdom .................. 9111973

[51] Int. Cl.$^6$ ..................... C07D 471/04; A01N 43/90
[52] U.S. Cl. .................. 504/246; 504/276; 546/121; 548/302.7
[58] Field of Search ................... 504/193, 197, 504/246, 277, 278, 746, 776; 548/110, 113, 302.7, 302.7; 546/14, 23, 121

[56] References Cited

U.S. PATENT DOCUMENTS 4,789,394  12/1988  Boehner et al. ................. 548/453
5,039,334  8/1991  Schaliner et al. ................. 548/453

FOREIGN PATENT DOCUMENTS 8287587  12/1987  Australia .
070389   6/1982   European Pat. Off. .
211805   7/1986   European Pat. Off. .
272594  12/1987   European Pat. Off. .
349748   5/1989   European Pat. Off. .
384973  12/1989   European Pat. Off. .
3643748 12/1986   Germany .
2150929  7/1985   United Kingdom .

OTHER PUBLICATIONS

Chem. Abstracts 97 (23):198202 and JP-A-57109769 (1980).
Chemical Substance Index p. 60172, col. 2 line 105 (1980).
Sumitomo Chem. Co. Ltd. Chem. Abstracts; vol. 98, No. 15; 126096c (1983).
Shimano et al. Chem. Abstract; vol. 101, No. 13, 110916q (1984).
Liebl et al. Chem. Abstract, vol. 107, No. 15; 134211f (1987).
Kogyo, Chem. Abstract, vol. 94, No. 19; 156735y (1981).
Kogyo, Chem. Abstract, vol. 94, No. 25; 208700b (1981).
Mitsubishi Chem. Co. Chem. Abstract, vol. 93, No. 5; 46672u (1980).
Wakabayashi et al. Chem. Abstract, vol. 85, No. 21; 160100r (1976).
Hisida et al. Chem. Abstract, vol. 89, No. 5; 43410p (1978).
Tsuruta et al. Chem. Abstract, vol. 92, No. 17; 141802z (1980).

*Primary Examiner*—Robert Gerstl
*Attorney, Agent, or Firm*—Lynn Marcus-Wyner; Allen E. Norris

[57]  ABSTRACT

This invention relates to novel 2-(2,4,5-substituted phenyl) hydantoin compounds, intermediates therefor, synthesis thereof, and the use of said compounds for combatting weeds.

16 Claims, No Drawings

HYDANTOIN COMPOUNDS

This is a continuation of application Ser. No. 07/808,247, filed Dec. 12, 1991, now abandoned.

This invention relates to novel 2-(2,4,5-substituted phenyl) hydantoin compounds, intermediates therefor, synthesis thereof, and the use of said compounds for combatting weeds.

More particularly, one aspect of this invention relates to compounds of the formula (I)

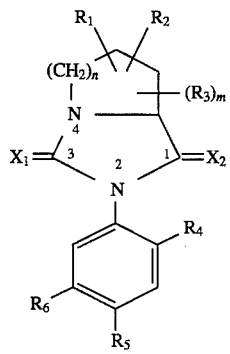

wherein $R_1$ is H, $C_{1-4}$alkyl, $C_{2-4}$alkenyl or halo;
$R_2$ is H or halo;
$R_3$ is OH, oxo, $C_{2-5}$alkanoyloxy, $C_{1-4}$alkylsulfonyloxy, $C_{1-4}$akoxy, $C_{2-4}$alkylenedioxy or halo;
$R_4$ is H or halo;
$R_5$ is halo, cyano or $C_{1-4}$alkyl;
$R_6$ is halo; $NO_2$; $NH_2$; CN; $C_{2-8}$alkynyl; $C_{2-8}$alkenyloxy, $C_{2-8}$alkynyloxy, $O(C_{1-4}$alkylene$)_k R_7$, or $S(C_{1-4}$alkylene$)_k R_7$, each of which is optionally substituted by CN or one or more halo; $C_{1-8}$alkyl optionally substituted with one or more groups selected from halo and CN; $C_{2-8}$alkenyl optionally substituted by one or more halo; $C_{2-5}$alkoxy carbonyl$C_{1-4}$alkyl, whereby the carbon atom of the alkyl group alpha to the alkoxycarbonyl group may be substituted with one more $C_{2-5}$alkoxycarbonyl group or a cyano group; $C_{2-5}$alkoxycarbonyloxy; $C_{2-5}$alkoxycarbonyl$C_{1-4}$alkoxy$C_{1-4}$-alkyl; $C_{2-5}$alkoxycarbonyl$C_{2-5}$alkenyl, whereby the alkenyl group is optionally substituted by halogen; $C_{1-4}$alkylthio$C_{1-4}$alkyl; $C_{1-4}$alkylsulfonyl$C_{1-4}$alkyl; $C_{1-4}$alkylsulfonyl; $C_{1-4}$alkylsulfonyloxy; $C_{1-4}$alkoxy$C_{1-4}$alkoxy; $OCH(SR_8)COOR_9$; $NR_{10}R_{11}$; $COOR_{12}$; $C(O)NR_{13}R_{13}'$; $C(O)R_{14}$; $R_{15}$; $CR_{14}(OC_{1-2}$alkyl$)_2$ or $CR_{14}(SC_{1-2}$alkyl$)_2$ whereby the alkyl groups optionally join together to form a ring; $CR_{14}=NOR_{13}$; thienyl$C_{1-4}$alkoxy wherein the thienyl is optionally halo substituted; or $C_{1-4}$alkoxy$C_{1-4}$alkoxycarbonyl;

or $R_5$ and $R_6$ join together with the phenyl ring to form a bicyclic ring containing nine to ten ring atoms, one to three of said ring atoms optionally being selected from oxygen, nitrogen and sulfur, and optionally being substituted with one or more groups selected from $C_{2-8}$alkynyl, halo, oxo, $C_{1-4}$alkylene-$R_{16}$, and $C_{2-8}$alkenyl and $C_{1-8}$alkyl which is itself optionally substituted by $C_{2-5}$alkoxycarbonyl, $C_{1-4}$alkoxy or CN;

$R_7$ is H; $C_{1-4}$alkyl, $C_{2-5}$alkenyl, $C_{2-5}$alkynyl, or $C_{3-8}$cycloalkyl, which hydrocarbyl is unsubstituted or substituted by one or more halo or by CN; cyclopentanonyl; phenyl optionally substituted by $O-C_{1-4}$alkylene-$COOR_8$; $C_{2-5}$alkanoyl; $C_{2-5}$alkoxycarbonyl wherein the alkoxy is optionally substituted by $C_{1-4}$alkylthio; $C(O)NR_8R_8'$; $C(=NOR_8)COOR_8'$; $P(O)(OR_8)OR_8'$; $R_{15}$; $C(O)R_{15}$; cyclopentoxycarbonyl; or phenoxy;

$R_8$ and $R_8'$ independently are $C_{1-4}$alkyl;

$R_9$ is $C_{1-4}$alkyl optionally substituted by one or more halo;
$R_{10}$ is H or $C_{1-4}$alkyl;
$R_{11}$ is H; $C_{1-4}$alkyl, optionally substituted by $P(O)(OR_8)R_8'$; $C_{2-5}$alkanoyl; $C_{2-5}$alkoxycarbonyl; or $C_{2-5}$alkoxycarbonyl$C_{1-4}$-alkyl;
$R_{12}$ is H; $C_{1-10}$alkyl; phenyl; an aromatic 5- or 6-membered ring comprising 1 to 3 heteroatoms selected from oxygen, sulphur and nitrogen; $N=C_{2-8}$alkylidene; or $C_{1-4}$alkyl substituted by one or more groups selected from $C_{1-10}$alkyl, cycloalkyl, $C_{2-10}$alkenyl, cycloalkenyl, $C_{2-10}$alkynyl, $NR_{10}R_{11}$, $C_{1-4}$alkylthio, CN, phenyl, an aromatic 5- or 6-membered ring comprising 1 to 3 heteroatoms selected from oxygen, sulphur and nitrogen, $C_{2-5}$alkanoyl, halo, $C_{1-4}$alkoxy, tri($C_{1-4}$alkyl)silyloxy, tri($C_{1-4}$alkyl)silyl, $C_{2-4}$alkoxycarbonyl, $P(O)(OR_8)OR_8'$, $C_{2-5}$alkanoyloxy, and di($C_{1-4}$alkyl)aminocarbonyloxy in which both alkyl groups may be tied together to form a saturated 5 to 6 membered heteroring optionally containing one further heteroatom selected from O, S and N, and in which any further N-heteroatom present may, depending on the hydrogenation degree of the heteroring, bear a hydrogen or a $C_{1-4}$alkyl group;
$R_{13}$ is H or $C_{1-4}$alkyl; and
$R_{13}'$ is H, $C_{1-4}$alkyl, $C_{1-4}$alkoxy, phenyl, CHO, $C_{2-5}$alkanoyl, $C_{1-4}$alkylsulfonyl, $C_{2-5}$alkoxycarbonyl$C_{1-4}$alkyl or $C_{2-5}$alkoxycarbonyl$C_{1-4}$alkoxy; or
$R_{13}$ and $R_{13}'$ together form a 5 to 6 membered heteroring optionally containing one or two further heteroatoms selected from O, S and N, whereby, depending on the hydrogenation degree of the heteroring, any further N-heteroatom may bear hydrogen or be substituted by $C_{1-4}$alkyl;
$R_{14}$ is H or $C_{1-4}$alkyl;
$R_{15}$ is a heterocyclic ring having 5 or 6 ring atoms, one to three of said ring atom being selected from oxygen, sulfur and nitrogen, which ring is optionally substituted with one or more groups selected from $C_{1-4}$alkyl and $C_{2-5}$alkoxycarbonyl;
$R_{16}$ is tetrahydropyranyl, 5,6-dihydro-2H-thiinyl, pyridyl, pyrazinyl, oxazolyl, or oxadiazolyl all of which are optionally substituted with $C_{1-4}$alkyl;
$X_1$ and $X_2$ are independently O or S;
k is 0 or 1; and
n and m are independently 1 or 2;
with the proviso that when $R_1$ and $R_2$ are H and m is 1, $R_3$ cannot be $C_{1-4}$alkoxy.

Any alkyl group in the compound of formula (I) may be branched or straight chain and preferably has one to four carbon atoms.

Any alkenyl or alkynyl group may be either branched or straight chain and preferably has two to five carbon atoms.

Halo as used herein, refers to Cl, F, Br or I.

Any cycloalkenyl group preferably has five to six carbon ring atoms.

Any cycloalkyl group preferably has three to five carbon ring atoms.

When $R_3$, $R_6$, $R_7$, $R_9$ or $R_{12}$ is substituted by halogen, it is preferably chlorine or fluorine, more preferably fluorine.

Where $R_5$ and $R_6$ join together with the phenyl ring to form a bicyclic ring, it is preferably an indanone; a benzazinone, particularly a quinolinone; a benzoxazinone; a benzodiazinone, particularly dihydroquinoxalinone; a benzothiazinone; a benzodioxane; a benzopyrane; a benzopyrone, particularly coumarin; a benzazole, particularly an indole, an indolone, an indazole, a benzotriazole, an isatine or a benzimidazolone; a benzoxazolone; a benzothiazolone; a benzofurane; or a benzdioxolane.

n is preferably 2. Where n is 2, preferably at least one $R_3$ is in the 7-position.

m is preferably 1.

$R_6$ is preferably $C_{1-4}$alkoxy, $C_{2-5}$alkenyloxy, $C_{2-5}$alkynyloxy, $C_{2-5}$haloalkenyl, $C_{2-5}$alkynyl or $COOR_{12}$, in which $R_{12}$ is as defined above. Typical examples of preferred $R_6$ significances include isopropoxy, methoxy, $O-CH(CH_3)-C\equiv CH$, $C\equiv CH$, $COOCH_3$, $COOCH(CH_3)_2$, $COOC(CH_3)_3$ and $COOCH(CH_2F)_2$. $R_6$ is more preferably $C_{1-4}$alkoxy.

$R_1$ is preferably hydrogen or halo, more preferably hydrogen.

$R_2$ is preferably hydrogen.

One of $R_3$ is preferably halo, more preferable fluoro or chloro particularly fluoro.

$R_4$ is preferably F.

$R_5$ is preferably $C_{1-4}$alkyl, halo or CN, particularly Cl.

A particularly preferred subgroup of compounds of the formula (I) are those in which $X_2$ is oxo, $R_1$ is H or halo, $R_2$ is H, $R_3$ is OH, halo or oxo, $R_4$ is F, $R_5$ is Cl, CN or Br, and $R_6$ is $C_{1-4}$alkoxy, $C_{2-5}$alkynyl, $C_{2-5}$alkoxycarbonyloxy, $C_{2-5}$alkoxycarbonyl, $C_{2-5}$alkoxycarbonyl$C_{1-4}$alkoxy, phenoxy$C_{1-4}$alkoxy, $C_{1-4}$alkoxy$C_{1-4}$alkoxy or $C_{1-4}$alkoxy$C_{1-4}$alkoxycarbonyl.

Compounds of the formula (I) are useful because they demonstrate herbicidal activity.

Compounds of the formula (I) can be obtained through the condensation reaction between the amide and the group $R_{17}$ of the compound of formula (II)

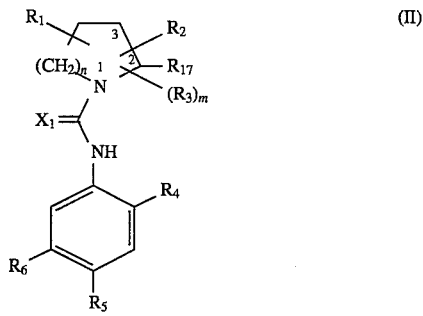

wherein $R_{1-6}$, $X_1$, n and m are as defined above;

$R_{17}$ is $C(X_2)OH$; $C(X_2)OW$; $COSW$; $COON=CWW'$; $CONHSO_2W$; $CONHOCH_2COOW$; $COOCHO_2COW$; $COOCHWOCOW'$; or $CONHOCH_2COOH$; and W and W' are independently $C_{1-8}$alkyl, $C_{2-8}$alkenyl, $C_{2-8}$alkynyl, or phenyl, each of which is optionally substituted by CN, $C_{1-4}$alkoxy or one or more halo.

This condensation reaction is carried out under conditions that are typical for preparing hydantoin compounds. The reaction is facilitated by the presence of an acid or an alkaline agent.

In cases where n is 1, the condensation reaction is preferably carried out under acidic conditions. Accordingly, the reaction may be carried out in an inert medium such as dioxane in the presence of an acid such as HCl. Suitable temperatures range from about room to reflux temperature, the preferred temperature being reflux. The desired end-product may be obtained from solution by known techniques such as distillation, crystallization and chromatographic methods.

In cases where n is 2, the condensation reaction may be carried out under acidic or alkaline conditions. Accordingly, the reaction may be carried out in an inert medium such as toluene in the presence of an alkaline agent such as triethylamine. Suitable temperatures range from about room to 60° C., preferably about 50° C. The resulting product is isolated and purified in accordance with known processes such as extraction and crystallization.

Compounds of the formula (II) are useful not only as intermediates in the production of compounds of the formula (I), but also because they themselves demonstrate herbicidal activity. Preferred groups n, m, and $R_{1-6}$ are as previously mentioned. Where W and/or W' is optionally substituted $C_{1-8}$alkyl it has preferably 1–4 carbon atoms. Where W and/or W' is optionally substituted $C_{2-8}$alkenyl or $C_{2-8}$alkynyl it has preferably 2 to 5 carbon atoms. $R_{17}$ is preferably COOH or $COOC_{1-4}$alkyl.

Compounds of the formula (II) may be prepared by reacting a compound of the formula (III)

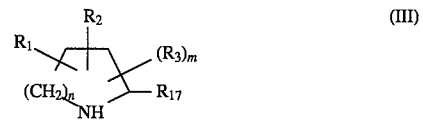

wherein $R_{1-3}$, $R_{17}$, n and m are previously defined with the desired substituted phenyl isocyanate or isothiocyanate. This reaction may be carried out in an inert medium such as toluene, preferably at ambient temperature. The resulting compound of formula (II) can be recovered from solution by standard separation techniques, e.g. suction filtration and chromatography.

The substituted phenyl isocyanates or isothiocyanates to be employed in the process for the preparation of the compounds of formula II are known. Compounds of the formula (III) are either known or can be prepared from known compounds according to known procedures.

Certain compounds of the formulae (I) and (II) wherein $R_3$ is other than OH are conveniently prepared by first preparing the corresponding compound wherein $R_3$= OH followed by the appropriate exchange of $R_3$ substituents, or, in the case of $R_3$= oxo, oxidation.

Thus, e.g., compounds of formulae (I) or (II) in which $R_3$= fluoro, oxo or acetoxy can be prepared by treating compounds of formulae (I) or (II) in which $R_3$ is OH with e.g. $SF_4$ or diethylaminosulphurtrifluoride (DAST), an oxidation agent such as dimethylsulfoxide/diphosgene or pyridinium chlorochromate, or acetic anhydride, respectively.

Further, compounds in which m= 2 and $R_3$ is F with both F attached to the same carbon atom can be prepared by treating the corresponding compound in which $R_3$= oxo with e.g. DAST or $SF_4$.

Regio-isomers of the formula I wherein n is 2, $R_1$ and $R_2$ are H and $(R_3)_m$ is 6-OH, 7-F or 6-F, 7-OH and wherein $R_{4-6}$, $X_1$ and $X_2$ are as previously defined can be prepared by treating a compound of the formula IV

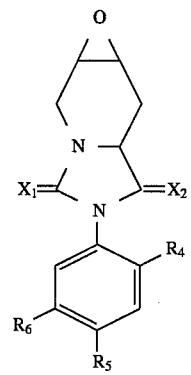

wherein $R_{4-6}$, $X_1$ and $X_2$ are as previously defined with e.g. triethylamine-tris-hydrofluoride. Compounds of the formula IV are either known or obtainable from known, analogous starting materials using known procedures.

The compounds of formulae (I) and (II) are effective in controlling the growth of plants. By plants it is meant germinating seeds, merging seedlings and established vegetation including underground portions. In particular, the compounds are useful as herbicides as indicated by causing damage to both monocotyledoneous and dicotyledoneous plants in various standard evaluations for determining such effects. The herbicidal effects are exhibited both pre- and post-emergence the plants. Such herbicidal effects indicate that the compounds of formulae (I) and (II) are particularly of interest in combatting weeds (unwanted plants).

The compounds of the formulae (I) and (II) are indicated mainly to be stronger acting against dicotyledoneous plants than monocotyledoneous plants. Relatively less toxicity towards crops than towards weeds is further indicated. Hence, the compounds are of particular interest as selective herbicides to combat weeds in a crop locus, particularly as locus of a crop such as, for example, sugarbeet, sunflower, cotton soybean, corn and wheat.

The present invention therefore also provides a method of combatting weeds in a locus which comprises applying to the weeds or their locus a herbicidally effective amount of a compound of the invention. When selective action is desired in crop locus, the amount applied will be sufficient to combat weeds without substantially damaging the crop.

For general herbicidal as well as selective herbicidal use of the compounds of the invention, the particular amounts to be applied will vary depending upon recognized factors such as the compound employed, the plants primarily in the locus, the timing, mode and formulation in application, the various conditions of treatment such as soil and weather and the like. However, in general, satisfactory results in weed control are usually obtained upon application of the compounds of the invention at a rate in the range of from 0.001 to 2 kg/hectare, more usually 0.01 to 1 kg/hectare, and preferably 0.01 to 0.25 kg/hectare, the application being repeated as necessary. When used in crops, the application usually will not exceed about 1 kg/hectare, and is usually in the range of 0.01 to 0.5 kg/hectare.

For practical use as herbicides, the compounds of formulae (I) and (II) may be and are preferably employed in herbicidal compositions comprising a herbicidal effective amount of the compound and an inert carrier which is agriculturally acceptable in the sense of not, by reason of its presence, poisoning the agricultural environment including the immediate soil of application or any crops present therein or otherwise being unsafe for application. Such compositions of formulations may contain 0.01% to 99% by weight of active ingredient, from 0 to 20% by weight of agriculturally acceptable surfactants and 1 to 99.99% by weight of the inert carrier. Higher ratios of surfactant to active ingredient are sometimes desirable and are achieved by incorporation into the formulation or by tank mixing. Application forms of composition typically contain between 0.01 and 25% by weight of active ingredient, but lower or higher levels of active ingredient can, of course, be present depending on the intended use and the physical properties of the compound. Concentrate forms of composition intended to be diluted before use generally contain between 2 and 90%, preferably between 10 and 80% by weight of active ingredient.

Useful compositions or formulations of the compounds of the invention include dusts, granules, pellets, suspension concentrates, wettable powders, emulsifiable concentrates and the like. They are obtained by conventional manner, e.g. by mixing the compounds of the invention with the inert carrier. More specifically, liquid compositions are obtained by mixing the ingredients, fine solid compositions by blending and, usually grinding, suspensions by wet milling and granules and pellets by impregnating or coating (preformed) granular carriers with the active ingredient or by agglomeration techniques.

For example, dusts can be prepared by grinding and blending the active compound with a solid inert carrier such as talc, clay, silica and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water or oil to any desired concentration of the active compound, can be prepared by incorporating wetting agents into concentrated dust compositions.

Alternatively, the compounds of the invention may be used in micro-encapsulated form.

Agriculturally acceptable additives may be employed in the herbicidal compositions to improve the performance of the active ingredient and to reduce foaming, caking and corrosion.

Surfactant as used herein means agriculturally acceptable material which imparts emulsifiability, spreading, wetting, dispersiblity or other surface-modifying properties properties. Examples of surfactants are sodium lignin sulphonate and lauryl sulphate.

Carriers as used herein mean a liquid or solid material used to dilute a concentrated material to a usable or desirable strength. For dusts or granules it can be e.g. talc, kaolin or diatomaeous earth, for liquid concentrate forms, a hydrocarbon such as xylene or an alcohol such as isopropanol; and for liquid application forms, e.g. water or diesel oil.

The compositions of this application can also comprise other compounds having biological activity, e.g. compounds having similar or complementary herbicidal ativity or compounds having antidotal, fungicidal or insecticidal activity.

Typical herbicidal composition, according to this invention, are illustrated by the following Examples A, B and C in which the quantities are in parts by weight.

EXAMPLE A

Preparation of a Dust

10 Parts of a compound of formulae (I) or (II) and 90 parts of powdered talc are mixed in a mechanical grinder-blender and are ground until a homogeneous, free-flowing dust of the desired particle size is obtained. This dust is suitable for direct application to the site of the weed infestation.

EXAMPLE B

Preparation of Wettable Powder

25 Parts of a compound of formulae (I) or (II) are mixed and milled with 25 parts of synthetic fine silica, 2 parts of sodium lauryl sulphate, 3 parts of sodium ligninsulphonate and 45 parts of finely divided kaolin until the mean particle size is about 5 micron. The resulting wettable powder is diluted with water before use to a spray liquor with the desired concentration.

EXAMPLE C

Preparation of Emulsifiable Concentrate (EC)

13 Parts of a compound of formulae (I) or (II) are mixed in a beaker with 7 parts of Toximul 360A (a mixture of anionic and non-ionic surfactants containing largely non-ionic surfctants), 24 parts of dimethylformamide and 56 parts of Tenneco 500-100 (predominantly a mixture of alkylated aromatics such as xylene and ethylbenzene) until solution is effected. The resulting EC is diluted with water for use.

FINAL COMPOUNDS

Unless otherwise indicated, temperatures herein stated are in Celsius.

EXAMPLE 1

2-[4-chloro-2-fluoro-5(isopropoxy)-phenyl]-7-hydroxy-tetrahydroimidazo{1,5a]-pyridine 1,3 (2H,5H)-dione.

545 mg (2.38 mmole) of solid, finely powdered 4-chloro-2-fluoro- 5-isopropoxyphenyl isocyanate are added with stirring to a solution of 380 mg (2.38 mmole) of 4-hydroxy-2-piperidine carboxylic acid methyl ester in 10 ml of anhydrous toluene.

The reaction solution is stirred at room temperature for a period of 3 hours and is then filtered by suction. The organic solvent is evaporated. The crude product is chromatographed on a silica gel column with hexane:ethyl acetate (4:1).

The title compound is obtained as a colorless powder with a m.p. of 156°–158° C. (compound 1.1, Table A).

EXAMPLE 2

2-[4-chloro-2-fluoro-5(isopropoxy)-phenyl]-7-fluoro-tetrahydroimidazo[1,5a]-pyridine 1,3 (2H,5H)-dione.

To a stirred solution of 2-[4-chloro-2-fluoro-5-(isopropoxy)phenyl]- 7-hydroxy-tetrahydro-imidazo[1,5a]-pyridine 1,3 (2H,5H)-dione (1 g, 2,8 mmole) in 20 ml anhydrous methylene chloride at −78° C. is added in one portion 1,36 ml of diethylaminosulphurtrifluoride (DAST). The reaction mixture is brought to room-temperature and stirred for 12 hours.

The reaction mixture is evaporated and purified on a silica gel column with hexane:ethyl acetate (1:1). The desired product is obtained as a liquid (compound 1.2, Table A), Rf= 0.42 (on silica gel with hexane-ethyl acetate 1:1).

EXAMPLE 3

2-[4-chloro-2-fluoro-5(isopropoxy)-phenyl]-tetrahydro-imidazo[1,5a]-pyridine- 1,3-(2H,5H)-7-trione.

To a stirred solution of 2-[4-chloro-2-fluoro-5(isopropoxy)phenyl]- 7-hydroxy-tetrahydro-imidazo[1,5a]-pyridine 1,3 (2H,5H)-dione (200 mg, 0.56 mmole) in 10 ml anhydrous methylene chloride at room temperature are added 270 mg (1,26 mmole) of pyridinium chlorochromate. Stirring is continued for 12 hours at room temperature. The reaction mixture is filtered over silica gel and then purified on a silica gel column.

Elution with ethyl acetate:hexane affords the title compound as a colourless powder with a m.p. of 63°–65° C. (compound 1.3, Table A).

EXAMPLE 4

2-[4-chloro-2-fluoro-5(isopropoxy)-phenyl]-7,7-difluoro-tetrahydroimidazo [1,5a]-pyridine-1,3-(2H,5H)-dione.

450 mg (2,8 mmole) of diethylaminosulphurtrifluoride are added to 500 mg (1,4 mmole) of 2-[4-chloro-2-fluoro-5(isopropoxy)phenyl]-tetrahydro-imidazo[ 1,5a]-pyridine-1,3,7-trione and stirred at room temperature for 2 hours. The reaction mixture is then diluted with methylene chloride and evaporated to dryness. The residue is chromatographed on a silica gel column with hexane:ethyl acetate (7:3) as eluent.

The title compound is then isolated as a colourless powder with m.p. of 107°–109° C. (compound 1.4, Table A).

EXAMPLE 5

Tetrahydro-2-[4-chloro-2-fluoro-5-isopropoxy)-phenyl]-6-hydroxy- 1-H-pyrrolo[1,2-c] imidazole-1,3(2H)-dione A solution of 1.4 g (3.74 m moles) of 1-[[4-chloro-2-fluoro-5-isopropoxyphenyl)amino]- 4-hydroxy pyrrolidine-2-carboxylic acid methyl ester in 15 ml of dioxane and 20 ml of 2N hydrochloric acid is refluxed for 1.5 hours and is then evaporated in vacuo (60°/20 torr).

The residue is taken up with 100 ml of methylene chloride and filtered. The residual syrup left on rotevaporation of the dried ($Na_2SO_4$) filtrate is chromatographed on a silica gel column. Elution with ethyl acetate furnishes the title compound as a viscous oil having a $R_f$: 0.57 (on silica gel with ethyl acetate) (compound 1.5, Table A).

Following the procedure of Example 5, compounds 1.6–1.53 of Table A, below are synthesized.

TABLE A

Compounds of the formula (I) in which $X_2$ is O, $R_2$ is H and $R_4$ is F.

| Compound No. | n | $X_1$ | $R_1$ | $R_6$ | $(R_3)_m$ | $R_5$ | m.p. or Rf on silica gel |
|---|---|---|---|---|---|---|---|
| 1.1 | 2 | O | H | isopropoxy | 7-OH | Cl | 156°–158° |
| 1.2 | 2 | O | H | isopropoxy | 7-F[1] | Cl | 0.42 (hexane:ethyl) acetate 1:1) |
| 1.3 | 2 | O | H | isopropoxy | 7-oxo | Cl | 63–65° |
| 1.4 | 2 | O | H | isopropoxy | 7,7-di-F | Cl | 107–109° |
| 1.5 | 1 | O | H | isopropoxy | 6-OH(6R,7aS) | Cl | 0.57 (ethyl acetate) |
| 1.6 | 1 | O | H | isopropoxy | 7-OH[2] | Cl | 175–176° C. |
| 1.7 | 2 | S | H | $CH_2C≡CH$ | 8-oxo | Cl | 199–201° |
| 1.8 | 2 | O | H | isopropoxy | B-OH[3] | Cl | 124–125° |
| 1.9 | 1 | O | H | isopropoxy | 6-F | Cl | 90–92° C.; 0,13 (hexane:ethyl-acetate 1:1) |
| 1.10 | 1 | O | H | isopropoxy | 7-F[4] | Cl | 0.25 (hexane:ethyl-acetate 1:2) |

TABLE A-continued

Compounds of the formula (I) in which $X_2$ is O, $R_2$ is H and $R_4$ is F.

| Compound No. | n | $X_1$ | $R_1$ | $(R_3)_m$ | R5 | R6 | m.p. or Rf or $SiO_2$ |
|---|---|---|---|---|---|---|---|
| 1.11 | 2 | O | H | -7OH | CN | isopropoxy | 206°–208° |
| 1.12 | 2 | O | H | -7F | CN | isopropoxy | 147°–149° |
| 1.13 | 2 | O | H | -7OH | Br | isopropoxy | 150°–152° |
| 1.14 | 2 | O | H | -7F | Br | isopropoxy | 0,32 (Hexane:ethyl-acetate 1:1) |
| 1.15 | 2 | O | H | -7OH | Cl | methoxy | 189°–191° |
| 1.16 | 2 | O | H | -7F | Cl | methoxy | 0,18 (hexane:ethyl-acetate 1:1) |
| 1.17 | 2 | O | H | -7OH | Cl | methoxy-carbonyloxy | 0,44 (ethylacetate 1:1) |
| 1.18 | 2 | O | H | -7F | Cl | methoxy-carbonyloxy | 0,23 (hexane:ethyl-acetate 1:1) |
| 1.19 | 2 | O | H | -7OH | Cl | hydroxy | 195°–198° |
| 1.20 | 2 | O | 6-Iodo | -7OH | Cl | isopropoxy | 56°–58° C. 0,27 (hexane:ethyl-acetate 1:1) |
| 1.21 | 2 | O | 6-bromo | -7Br | Cl | isopropoxy | 0,50 (hexane:ethyl-acetate 2:1) |
| 1.22 | 2 | O | H | 6-OH | Cl | isopropoxy | 0,15 (hexane:ethyl-acetate 4:6) |

| Compound No. | n | $X_1$ | $R_1$ | $R_3$ | $R_5$ | $R_6$ | m.p. or Rf or $SiO_2$ |
|---|---|---|---|---|---|---|---|
| 1.23 | 2 | O | H | 6-F | Cl | isopropoxy | 0,41 (hexane: ethyl-acetate 4:6) |
| 1.24 | 2 | O | H | 6-oxo | Cl | isopropoxy | 0,20 (hexane:ethyl-acetate 4:6) |
| 1.25 | 2 | O | H | 6,6-diF | Cl | isopropoxy | 0,30 (hexane:ethyl-acetate 4:6 |

| Compd. No. | n | $X_1$ | $R_1$ | $R_6$ | $(R_3)_m$ | $R_5$ | m.p. or Rf on silical gel |
|---|---|---|---|---|---|---|---|
| 1.26 | 2 | O | H | isopropoxy | 7-OH[1] | Cl | 0,32 (ethyl acetate) |
| 1.27 | 2 | O | H | isopropoxy | 7-F[3] | Cl | 0,30 (hexane:ethyl acetate 1;1) |
| 1.28 | 2 | O | H | methoxy | 7-F[3] | Cl | 0,18 (hexane:ethyl acetate 1:1) |
| 1.29 | 2 | O | H | —O—CH(CH$_3$)—CH≡CH | 7-OH | Cl | 0,30 (ethyl acetate) |
| 1.30 | 2 | O | H | —O—CH(CH$_3$)—CH≡CH | 7-F | cl | 166-168° |
| 1-31 | 2 | O | H | methoxy | 7-oxo | Cl | 0,24 (hexane:ethyl acetate 3:7) |
| 1.32 | 2 | O | H | methoxy | 7,7-di-F | Cl | 0,17 (hexane: ethyl acetate 1:1) |
| 1.33 | 2 | O | H | —C(O)—OCH(CH$_3$)$_2$ | 7-OH | cl | 169-171° |
| 1.34 | 2 | O | H | —C(O)—OCH(CH$_3$)$_2$ | 7-F | Cl | 0,40 (hexane:ethyl acetate 1:1) |
| 1.35 | 2 | O | H | —C(O)—OCH(CH$_3$)$_2$ | 7-oxo | el | 0,40 (hexane:ethyl acetate 3:7) |
| 1.36 | 2 | O | H | —C(O)—OCH(CH$_3$)$_2$ | 7,7-di-F | Cl | 0,33 (hexane:ethyl acetate 7:3) |
| 1.37 | 2 | O | H | —O—CH(CH$_3$)—C(O)OCH3 | 7-OH[3] | Cl | 0,33 (ethyl acetate acetone 9:1) |
| 1.41 | 2 | O | H | —O—CH(CH$_3$)—C(O)OCH3 | 7-OH[1] | Cl | 0,26 (ethyl acetate: acetone 9:1) |
| 1.39 | 2 | O | H | —O—CH(CH$_3$)—C(O)OCH3 | 7-F | Cl | 0,25 (ethyl acetate; hexane 1:1) |
| 1.40 | 2 | O | 6-Iodo | isopropoxy | 7-F | Cl | 0,41 (hexane; ethyl acetate 1:1) |
| 1.41 | 2 | O | H | —O-(CH$_2$)—O—C$_6$H$_5$ | 7-OH | Cl | 0,30 (ethyl acetate) |
| 1.42 | 2 | O | H | —O-(CH$_2$)$_2$—O—C$_6$H$_5$ | 7-F[3] | Cl | 0,24 (hexane:ethyl acetate 1:1) |
| 1.43 | 2 | O | H | —O-(CH$_2$)$_2$—O—C$_6$H$_5$ | 7-F[1] | Cl | 0,28 (hexane:ethyl acetate 1.1) |
| 1.44 | 2 | O | H | —C(O)O—CH(CH$_3$)—CH$_2$—OCH$_3$ | 7-OH | Cl | 0,26 (hexane:ethyl acetate 1:1) |
| 1.45 | 2 | O | H | —C(O)O—CH(CH$_3$)—CH$_2$—OCH$_3$ | 7-OH[3] | Cl | 0,20 (hexane:ethyl acetate 1:1) |
| 1.46 | 2 | O | H | —C(O)O—CH(CH$_3$)—CH$_2$—OCH$_3$ | 7-F[3] | Cl | 0,16 (hexane:ethyl acetate 1:1) |
| 1.47 | 2 | O | H | —C(O)O—CH(CH$_3$)—CH$_2$—OCH$_3$ | 7-F[1] | Cl | 0,24 (hexane:ethyl acetate 1:1) |
| 1.48 | 2 | O | H | 5—Cl-thien-2-yl-methoxy | 7,7-diF | Cl | |
| 1.49 | 2 | O | H | 5—Cl-thien-2-yl-methoxy | 7-F | Cl | |
| 1.50 | 2 | O | H | ethoxymethoxy | 7,7-di-F | Cl | |
| 1.51 | 2 | O | H | ethoxymethoxy | 7-F | Cl | |
| 1.52 | 2 | O | H | —C(O)O—CH(CH$_3$)$_3$ | 7-OH | Cl | 154–155° |
| 1.53 | 2 | O | B | —C(O)O—CH(CH$_3$)$_3$ | 7-F | Cl | 0.43 (hexane:diethylether 1:1) |

[1]trans with respect to the 8a position
[2]cis with respect to the 7a position
[3]cis with respect to the 8a position
[4]trans with respect to the 7a position

REGIO-ISOMERS

EXAMPLE 6

2-Chloro-4-fluoro-5-(hexahydro-1,3-dioxo-imidazo-[1,5a]-7-fluoro-6-hydroxy-pyridin- 2(3H)-yl-benzoic acid-1-methyl-ethyl ester and
2-Chloro-4-fluoro-5-(hexahydro-1,3-dioxo-imidazo-[1,5a]-6-fluoro-7-hydroxy-pyridin- 2(3H)-yl-benzoic acid-1-methyl ethyl ester (compounds of the formula Ia and Ib wherein $X_1$ and $X_2$ are oxygen, $R_4$ is F, $R_5$ is Cl and $R_6$ is isopropoxycarbonyl)

The heterogenous mixture of 2.7 g (0.007 mol) of 2-chloro-4-fluoro-5-(hexahydro-1,3-dioxo-imidazo-[1,5a]-6,7-epoxypyridin- 2(3H)-yl)-benzoic acid-1-methylethyl ester and 1.2 ml (0.0074 mol) of triethylamine-tris-hydrofluoride is stirred, under a nitrogen atmosphere, 16 hours at 110°.

The dark brown reaction mixture is then cooled to ambient, dissolved in methylene chloride (200 ml), washed with 10% $NaHCO_3$ solution (100 ml), two 100 ml portions of water, dried ($Na_2SO_4$) and evaporated in vacuo.

The resulting crude mixture of the two title compounds is separated by chromatography with hexane-ethyl acetate as the mobile phase: first eluted (hexane-ethyl acetate 3:2) is the 2-chloro-4-fluoro-5-(hexa-hydro-1,3-dioxoimidazo-[1,5a]-7-fluoro-6-hydroxy-pyridin- 2 (3H)-yl) benzoic acid-1-methylethyl ester; $R_f$= 0.38 with ethyl acetate hexane 2:1 on silica gel.

Continued elution of the silica gel column (hexane ethylacetate 1:2) affords the regio-isomeric compound, having a m.p. of 134°.

INTERMEDIATES

EXAMPLE 7

1[[(4-chloro-2-fluoro-5-isopropoxyphenyl)amino]-carbonyl]-(2R)-4-oxopyrrolidine- 2-carboxylic acid methyl ester To the cooled (–65°) solution of 1,15 g (0,0058 moles) of trichloromethyl chloroformate in 30 ml of dry $CH_2Cl_2$ are added dropwise with stirring 1,65 g (0,021 moles) of dimethyl sulfoxide.

After the addition is complete, the reaction mixture is stirred for a further 5 minutes at –70° and then treated—at the same temperature—with the solution of 2,03 g (0,054 moles) of 1[[(4-chloro-2-fluoro-5-isopropoxyphenyl)amino] carbonyl]-cis-4-hydroxy-D-proline methyl ester in 50 ml of dry $CH_2Cl_2$. After all the proline ester has been added, the reaction mixture is kept at –65° for 15 minutes and is then treated with 3,6 ml (0,026 moles) of triethylamine.

Then the solid $CO_2$/acetone bath is removed the reaction mixture allowed to warm to 17° (50 min) and treated with 75 ml of water. The organic layer is separated, washed with two 120 ml portions of water and dried ($Na_2SO_4$).

The dark brown syrup left on rotevaporation of the methylene chloride is chromatographed on a silica gel column.

Elution with diethyl ether—hexane (1:1) affords the title compound as a yellowish viscous liquid, $R_f$= 0,35 (on silica gel with diethyl ether) (compound 2.1, Table B).

EXAMPLE 8

1[[(4-chloro-2-fluoro-5-isopropoxyphenyl)amino]-carbonyl]-(2R)-4-cis-acetoxypyrrolidine-2-carboxylic acid methyl ester 3,75 g (0,01 mol) of 1[[(4-chloro-2-fluoro-5-isopropoxyphenyl)amino] carbonyl]-cis-4-hydroxy-D-proline methyl ester are dissolved in the mixture of 5 ml of acetic anhydride and 5 ml of pyridine.

Upon standing for 20 hours at room temperature, the reaction solution is evaporated in vacuo (60°/20 torr). The residue is taken up with $CH_2Cl_2$ and washed successively with 50 ml of 5% $H_2SO_4$, 50 ml of water, 30 ml of saturated $NaHCO_3$ solution and again with water (75 ml). The residual viscous oil left on rotevaporation of the dried ($Na_2SO_4$) methylene chloride, solidifies completely on chilling overnight at –20°: m.p. 92° (triturated with diethylether-hexane (1:9)) (compound 2.2, Table B).

EXAMPLE 9

1[[(4-chloro-2-fluoro-5-isopropoxy) phenyl]aminocarbonyl]-( 2S)-4-trans-hydroxy-pyrrolidine-2-carboxylic acid methyl ester.

6.91 g (30.12 mmole) of solid finely powdered 4-chloro-2-fluoro-5-isopropoxyphenyl isocyanate are added in single portions with stirring to a solution of 4.37 g (30.10 mmol) of trans-4-hydroxy-L-proline methyl ester in 20 ml of anhydrous toluene solution.

The reaction solution is stirred at room temperature for a period of 12 hours and is then filtered by suction. The organic solvent is evaporated. The crude product is crystallised from ethyl acetate/hexane as colourless crystals with a m.p. of 136°–138° C. (Compound 2,3, Table B).

EXAMPLE 10

1-[[(4-chloro-2-fluoro-5-isopropoxy) phenyl] aminocarbonyl]-( 2S)-4-cis-fluoro pyrrolidine-2-carboxylic acid methyl ester To a stirred solution of 1,27 ml (10,4 m mole) of diethylaminosulphurtrifluoride (DAST) in 20 ml anhydrous methylene chloride at –78° C. is added a chilled solution of 1 g (2,6 m mole) of 1[[(4-chloro- 2-fluoro-5-isopropoxy)phenyl]aminocarbonyl]-(2S)-4-trans-hydroxy-pyrrolidine-2-carboxylic acid methyl ester. The reaction mixture is stirred further for two hours at –78° C. and then brought to room-temperature and stirred further for 12 hours at this temperature. The reaction mixture is evaporated and purified on a silica gel column with hexane: ethyl acetate (3:1). The desired product is obtained as a liquid having $R_f$=0.13 (hexane:ethyl acetate 3:1) (Compound 2.4, Table B).

EXAMPLE 11

1[[4-chloro-2-fluoro-5-isopropoxyphenyl)amino]-carbonyl]-(2R)-4-cis-hydroxypyrrolidine-2-carboxylic acid methyl ester.

To a stirred solution of 4,2 g (0,029 moles) of cis-4-hydroxy-D-proline methyl ester in 50 ml of dry toluene are added dropwise without cooling 6,7 g (0,029 moles) of 4-chloro-2-fluoro-5-isopropoxyphenyl isocyanate, dissolved in 250 ml of dry toluene.

After the exothermic reaction (28°) has subsided, the reaction mixture is stirred 4 hours longer at ambient temperature and is then taken to dryness.

The residue is chromatographed on a silica gel column.

Elution with ethyl acetate affords the title compound as a yellowish syrup ($R_f$= 0,33 on silica gel with ethyl acetate) which exhibits satisfactory spectral properties (Compound 2.5, Table B).

Following the procedure for Compound 2.3, Compounds 2.5–2.14 are synthesized.

TABLE B

Compounds of the formula (II) in which $R_1$ and $R_2$ are H, $R_4$ is F and $R_5$ is Cl.

| Comp. No. | n | $X_1$ | $R_6$ | $(R_3)_m$ | $R_{17}$ | m.p. or $R_f$ on silica |
|---|---|---|---|---|---|---|
| 2.1 | 1 | O | isopropoxy | 4-oxo | COOCH₃ | 0.35 (diethyl ether) |
| 2.2 | 1 | O | isopropoxy | 4-acetoxy | COOCH₃ | 92° |
| 2.3 | 1 | O | isopropoxy | 4-OH(4trans/2S)* | COOCH₃ | 136–141° |
| 2.4 | 1 | O | isopropoxy | 4-F(4cis/2S)* | COOCH₃ | 0.13 (hexane:ethyl acetate 3:1) |
| 2.5 | 1 | O | isopropoxy | 4-OH(4cis/2R)* | COOCH₃ | 0.33 (ethyl acetate) |
| 2.6 | 1 | O | methyl | 3-OH(3cis)* | COOCH₃ | |
| 2.7 | 1 | O | OCH₂C≡CH | 3-OH(3cis)* | COOCH₃ | |
| 2.8 | 1 | O | isopropoxy | 3-OH(3cis)* | COOCH₃ | |
| 2.9 | 2 | O | isopropoxy | 3-oxo | COOC₂H₅ | 0.44 (diethyl ether) |
| 2.10 | 1 | S | isopropoxy | 3-OH(3cis)* | COOCH₃ | |
| 2.11 | 2 | O | isopropoxy | 3-OH(3cis)* | COOH | 0.1 (CH₂Cl₂-CH₃OH 9:1) |
| 2.12 | 1 | O | isopropoxy | 3-OH(3cis)* | COOH | 153–154° C. |
| 2.13 | 1 | O | isopropoxy | 3-Cl(3cis)* | COOH | 158–159° C. |
| 2.14 | 1 | O | OCH₂≡CH | 3-Cl(3cis)* | COOH | 162–163° C. |

*the geom. configuration is with respect to group $R_{17}$.

What is claimed is:

1. A compound of the formula (I)

wherein $R_1$ is H, $C_{1-4}$alkyl, $C_{2-4}$alkenyl or halo;

$R_2$ is H or halo;

$R_3$ is OH, oxo, or halo;

$R_4$ is H or halo;

$R_5$ is halo, cyano or $C_{1-4}$alkyl;

$R_6$ is halo; $NO_2$; $NH_2$; CN; $C_{2-8}$alkynyl; $C_{2-8}$alkenyloxy; $C_{2-8}$alkynyloxy; $S(C_{1-4}$alkylene$)_kR_7$, optionally substituted by CN; $C_{1-8}$alkyl, optionally substituted with one or more groups selected from halo and CN; $C_{2-8}$alkenyl, optionally substituted by one or more halo; $C_{2-5}$alkoxycarbonyl$C_{1-4}$alkyl, whereby the carbon atom of the alkyl group alpha to the alkoxycarbonyl group may be substituted with one or more $C_{2-5}$alkoxycarbonyl group or a cyano group; $C_{2-5}$alkoxycarbonyloxy; $C_{2-5}$alkoxycarbonylC$_{1-4}$alkoxyC$_{1-4}$alkyl; $C_{2-5}$alkoxycarbonylC$_{2-5}$alkenyl, whereby the alkenyl group is optionally substituted by halogen; $C_{1-4}$alkylthioC$_{1-4}$alkyl; $C_{1-4}$alkylsulfonylC$_{1-4}$alkyl; $C_{1-4}$alkylsulfonyl; $C_{1-4}$alkylsulfonyloxy; $OCH(SR_8)COOR_9$; $NR_{10}R_{11}$; $COOR_{12}$; $C(O)NR_{13}R_{13}$; $C(O)R_{14}$; $R_{15}$; $CR_{14}(OC_{1-2}alkyl)_2$ or $CR_{14}(SC_{1-2}alkyl)_2$; $CR_{14}=NOR_{13}$; thienylC$_{1-4}$akoxy, wherein the thienyl is optionally halo substituted; or $C_{1-4}$alkoxyC$_{1-4}$alkoxycarbonyl;

or $R_5$ and $R_6$ join together to form a 5- or 6-membered ring, one to three of said ring atoms optionally selected from oxygen, nitrogen and sulfur and together with the phenyl ring to which they are attached form a bicyclic ring optionally being substituted with one or more groups selected from $C_{2-5}$alkynyl, halo, oxo, $C_{1-4}$alkylene-$R_{16}$, $C_{2-5}$alkenyl and $C_{1-8}$alkyl which is itself optionally substituted by $C_{2-5}$alkoxycarbonyl, $C_{1-4}$alkoxy or CN;

$R_7$ is H; $C_{1-4}$alkyl, $C_{2-5}$alkenyl, $C_{2-5}$alkynyl, or $C_{3-8}$cycloalkyl, which hydrocarbyl is unsubstituted or substituted by one or more halo or by CN; cyclopentanonyl; phenyl optionally substituted by O-$C_{1-4}$alkylene-COOR$_8$; $C_{2-5}$alkanoyl; $C_{2-5}$alkoxycarbonyl wherein the alkoxy is optionally substituted by $C_{1-4}$alkylthio; $C(O)NR_8R_8$; $C(=NOR_8)COOR_9$; $P(O)(OR_8)OR_8$; $R_{15}$; $C(O)R_{15}$; cyclopentaoxycarbonyl; or phenoxy;

$R_8$ and $R_8$. independently are $C_{1-4}$alkyl;

$R_9$ is $C_{1-4}$alkyl optionally substituted by one or more halo;

$R_{10}$ is H or $C_{1-4}$alkyl;

$R_{11}$ is H; $C_{1-4}$alkyl, optionally substituted by $P(O)(OR_8)R_8$.; $C_{2-5}$alkanoyl; $C_{2-5}$alkoxycarbonyl; or $C_{2-5}$alkoxycarbonylC$_{1-4}$alkyl;

$R_{12}$ is H; $C_{1-10}$alkyl; phenyl; an aromatic 5- or 6-membered ring comprising 1 to 3 heteroatoms selected from oxygen, sulphur and nitrogen N=$C_{2-8}$alkylidene; or $C_{1-4}$alkyl substituted by one or more groups selected from $C_{1-10}$alkyl, cycloalkyl, $C_{2-10}$alkenyl, cycloalkenyl, $C_{2-10}$alkynyl, $NR_{10}R_{11}$, $C_{1-4}$alkylthio, CN, phenyl, an aromatic 5- or 6-membered ring comprising 1 to 3 heteroatoms selected from oxygen, sulphur and nitrogen, $C_{2-5}$alkanoyl, halo, $C_{1-4}$alkoxy, tri($C_{1-4}$alkyl)silyloxy, tri($C_{1-4}$alkyl)silyl, $C_{2-5}$ alkoxycarbonyl, $P(O)(OR_8)OR_{8'}$, $C_{2-5}$alkanoyloxy, and di($C_{1-4}$alkyl)aminocarbonyloxy in which both alkyl groups may be tied together to form a saturated 5- to 6-membered heteroring one to three of the heteroatoms optionally selected from O, S and N, and any N-heteroatom optionally substituted with a hydrogen or a $C_{1-4}$alkyl group;

$R_{13}$ is H or $C_{1-4}$alkyl; and $R_{13'}$ is H, $C_{1-4}$alkyl, $C_{1-4}$alkoxy, phenyl, CHO, $C_{2-5}$-alkanoyl, $C_{1-4}$alkylsulfonyl, $C_{2-5}$alkoxycarbonyl$C_{1-4}$alkyl or $C_{2-5}$akoxycarbonyl$C_{1-4}$alkoxy; or $R_{13}$ and $R_{13'}$ together form a 5- to 6-membered heteroring optionally containing one or two heteroatoms selected from O, S and N, and any N-heteratom optionally substituted by $C_{1-4}$alkyl;

$R_{14}$ is H or $C_{1-4}$alkyl;

$R_{15}$ is a heterocyclic ring having 5 or 6 ring atoms, one to three of said ring atom being selected from oxygen, sulfur and nitrogen, which ring is optionally substituted with one or more groups selected from $C_{1-4}$alkyl and $C_{2-5}$alkoxycarbonyl;

$R_{16}$ is tetrahydropyranyl, 5,6-dihydro-2H-thiinyl, pyridyl, pyrazinyl, oxazolyl, or oxadiazolyl all of which are optionally substituted with $C_{1-4}$alkyl;

$X_1$ and $X_2$ are independently O or S;

k is 0 or 1; and n and m are independently 1 or 2.

2. The compound of formula (I)

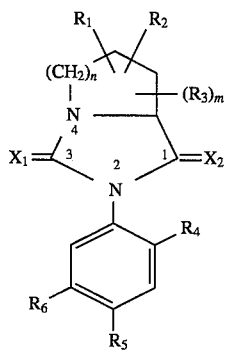

wherein $X_1$ and $X_2$ are oxo;

$R_1$ is H or halo;

$R_2$ is H;

$R_3$ is OH, halo, or oxo;

$R_4$ is F;

$R_5$ is halo, cyano or $C_{1-4}$alkyl;

$R_6$ is $C_{1-4}$alkoxy, $C_{2-5}$alkynyl, $C_{2-5}$alkoxycarbonyloxy, $C_{2-5}$alkoxycarbonyl, $C_{2-5}$ alkoxycarbonyl$C_{1-4}$alkoxy, phenoxy$C_{1-4}$alkoxy, $C_{1-4}$alkoxy$C_{1-4}$alkoxycarbonyl, $C_{2-5}$ alkoxycarbonyl$C_{1-4}$alkyl; whereby the carbon atom of the alkyl group alpha to the alkoxycarbonyl group may be substituted with one or more $C_{2-5}$alkoxycarbonyl group or a cyano group, or $C_{2-5}$alkoxycarbonyl$C_{2-5}$alkenyl; whereby the alkenyl group is optionally substituted by halogen; and n and m are independently 1 or 2.

3. The compound of formula (I) according to claim 2 wherein $R_3$ is F, $R_5$ is Cl and m is 1.

4. The compound of formula (I) according to claim 2 wherein $R_1$ is H; $R_3$ is halo; $R_6$ is $C_{1-4}$alkoxy; and n is 2.

5. The compound of formula (I) according to claim 1 wherein $R_3$ is F, $R_5$ is Cl and m is 1.

6. The compound of formula (I) according to claim 2 wherein $R_3$ is 7-F and $R_6$ is isopropyl.

7. The compound of formula (I) according to claim 1 wherein $R_1$ is H or halo;

$R_2$ is H;

$R_3$ is OH, halo, or oxo;

$R_4$ is F;

$R_5$ is Cl, CN, Br or $C_{1-4}$alkyl;

$X_1$ and $X_2$ are oxo;

n is 1 or 2 and $R_6$ is halo; $NO_2$; CN; $C_{2-8}$alkynyl; $C_{2-8}$alkenyloxy; $C_{2-8}$alkynyloxy; $S(C_{1-4}$alkylene$)_kR_7$, optionally substituted by CN; $C_{1-8}$alkyl, optionally substituted with one or more groups selected from halo and CN; $C_{2-8}$alkenyl, optionally substituted by one or more halo; $C_{2-5}$alkoxycarbonyl$C_{1-4}$alkyl, whereby the carbon atoms of the alkyl group alpha to the alkoxycarbonyl group may be substituted with one or more $C_{2-5}$alkoxycarbonyl group or a cyano group; $C_{2-5}$alkoxycarbonyloxy; $C_{2-5}$alkoxycarbonyl$C_{1-4}$alkoxy$C_{1-4}$alkyl; $C_{2-5}$alkoxycarbonyl$C_{2-5}$alkenyl, whereby the alkenyl group is optionally substituted by halogen; $C_{1-4}$alkylthio$C_{1-4}$alkyl; $C_{1-4}$alkylsulfonyl$C_{1-4}$alkyl; $C_{1-4}$alkylsulfonyl; $C_{1-4}$alkylsulfonyloxy; $OCH(SR_8)COOR_9$; $NR_{10}R_{11}$; $COOR_{12}$; $C(O)NR_{13}R_{13'}$; $C(O)R_{14}$; $R_{15}$; $CR_{1-4}(OC_{1-2}$alkyl$)_2$ $_1$ $_{or}$ $_{CR14}(SC_{1-2}$alkyl$)_2$; $CR_{14}=NOR_{13}$; thienyl$C_{1-4}$alkoxy wherein the thienyl is optionally halo substituted; or $C_{1-4}$alkoxy$C_{1-4}$alkoxycarbonyl.

8. The compound of formula (I) according to claim 7 wherein $R_1$ is H, $R_5$ is Cl, and $R_6$ is $C_{1-4}$alkoxy, $C_{2-5}$alkynyloxy, $C_{2-5}$haloalkenyl, $C_{2-5}$alkynyl and $COOR_{12}$.

9. The compound of formula (I) according to claim 7 wherein $R_1$ is H; $R_3$ is F; $R_5$ is Cl; and m is 1.

10. The compound of formula (I) according to claim 7 wherein n is 1.

11. A herbicidal composition comprising a herbicidally effective amount of a compound as defined in claim 1 and an agriculturally acceptable carrier.

12. A herbicidal composition comprising a herbicidally effective amount of a compound as defined in claim 7 and an agriculturally acceptable carrier.

13. A herbicidal composition comprising a herbicidally effective amount of a compound as defined in claim 2 and an agriculturally acceptable carrier.

14. A method of combatting weeds which comprises applying to the weeds or their locus a herbicidally effective amount of a compound as defined in claim 2.

15. A compound of Formula (I):

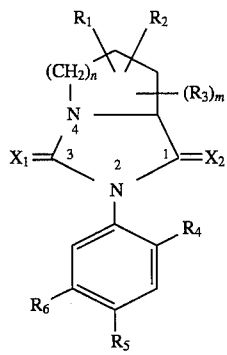

wherein $R_1$ is H, $C_{1-4}$alkyl, $C_{2-4}$alkenyl or halo;

$R_2$ is H or halo;

$R_3$ is OH, oxo, $C_{2-5}$alkanoyloxy, $C_{1-4}$alkylsulfonyloxy, $C_{2-4}$alkylenedioxy or halo;

$R_4$ is H or halo;

$R_5$ and $R_6$ together with the phenyl ring to which they are attached form an optionally substituted indanone, benzazinone, benzoazinone, benzoxazinone, benzothiazinone, benzodioxane, benzopyrene, benzopyrone, benzazole, benoxzolone, benzothiazolone, benzofurane, or benzodioxolane wherein said substituents are independently selected from the group $C_{2-8}$alkynyl, halo, oxo, $C_{1-4}$alkylene-$R_{16}$, $C_{2-8}$ alkenyl and $C_{1-8}$alkyl which is itself optionally substituted by $C_{2-5}$alkoxycarbonyl, $C_{1-4}$ alkoxy or CN;

$R_{16}$ is tetrahydropyranyl, 5,6-dihydro- 2H-thiinyl, pyridyl, pyrazinyl, oxazolyl or oxadiazolyl all of which are optionally substituted with $C_{1-4}$alkyl;

$X_1$ and $X_2$ are independently O or S;

k is 0 or 1, and m and n are independently 1 or 2.

16. A herbicidal composition comprising a herbicidally effective amount of a compound as defined in claim 15 and an agriculturally acceptable carrier.

* * * * *